United States Patent [19]

Feldman et al.

[11] 4,170,227
[45] Oct. 9, 1979

[54] APPARATUS AND METHOD FOR ECG BASELINE SHIFT DETECTING

[75] Inventors: Charles L. Feldman; Mark Hubelbank, both of Sudbury, Mass.

[73] Assignee: Electronics for Medicine, Inc., White Plains, N.Y.

[21] Appl. No.: 917,877

[22] Filed: Jun. 22, 1978

Related U.S. Application Data

[63] Continuation-in-part of Ser. No. 754,538, Dec. 27, 1976, Pat. No. 4,112,930.

[51] Int. Cl.² .............................................. A61N 5/04
[52] U.S. Cl. .................................................. 128/704
[58] Field of Search .................. 128/2.06 A, 2.06 B, 128/206 E, 2.06 F, 2.06 G, 2.06 R, 2.06 V, DIG. 4

[56] References Cited

U.S. PATENT DOCUMENTS

| | | | |
|---|---|---|---|
| 3,212,496 | 10/1965 | Preston | 128/2.06 R |
| 3,559,193 | 1/1971 | Savaglio et al. | 128/2.06 B |
| 3,608,543 | 9/1971 | Longini et al. | 128/DIG. 4 |
| 3,699,948 | 10/1972 | Ota et al. | 128/2.06 G |
| 3,868,947 | 3/1975 | Holsinger | 128/2.06 B |
| 3,903,874 | 9/1975 | Shakespeare | 128/2.06 A |

*Primary Examiner*—William E. Kamm
*Attorney, Agent, or Firm*—Charles Hieken

[57] ABSTRACT

In an electrocardiographic system there is a multielement electrode at two skin locations for providing an ECG signal of negligible magnitude between elements because of the close spacing while the pair of elements are sufficiently separated so that the motion of one element is at least partially independent of the motion of the other. Parallel ECG signals are obtained from different elements of two multielement electrodes. The difference between the signals is detected by logical circuitry to produce a signal indicating baseline shift.

6 Claims, 2 Drawing Figures

APPARATUS AND METHOD FOR ECG BASELINE SHIFT DETECTING

REFERENCE TO PRIOR COPENDING APPLICATION

This is a continuation-in-part of application Ser. No. 754,538, filed Dec. 27, 1976 now U.S. Pat. No. 4,112,930.

BACKGROUND OF THE INVENTION

The present invention relates in general to detecting the shift in the baseline in an electrocardiogram (ECG) and more particularly concerns a novel system using a multiple element electrode at a single measuring location with means for detecting potential differences between elements to reliably detect the occurrence of a baseline shift, thereby preventing automatic monitoring equipment from indicating an alarm condition about a patient being monitored when an alarm condition should not be indicated. The apparatus is relatively easy to fabricate and install, adds relatively little cost to the system and operates relatively reliably with little attention from maintenance personnel.

Automatic ECG monitoring systems, whether using simple rate alarms on a bedside monitor or more complex arrhythmia detectors, produce erroneous results at times because of the presence of a non-ECG artifact, consisting of a combination of high frequency "muscle noise" and lower frequency "baseline shift". The present invention is concerned with detecting baseline shift; that is, a shift in the average value of the ECG signal over a waveform portion.

The usual cause of "baseline shift" is physical manipulation of the electrodes or the skin and muscle underlying electrodes which may result from movement of an electrode, pressing of the surfaces as a result of patient movement, tugging upon the electrode lead and other causes. Good preparation of the skin surface to which the electrode is attached helps minimize baseline shift but does not eliminate it. As an example of one approach to dealing with this problem reference is made to U.S. Pat. No. 3,905,364 entitled *ARTIFACT DETECTOR*.

The prior art includes a number of patents on electrodes and multiple electrode systems. In the prior art multiple electrode systems, multiple electrodes or multielement electrodes are used to derive better estimates of the signal or to provide flexibility. Some multiple electrode systems are used to achieve rapid applications in emergency situations.

Prior art artifact detecting systems exemplified by Cudahy U.S. Pat. No. 3,905,364, Horth U.S. Pat. No. 3,552,386 and Vandenberg U.S. Pat. No. 3,050,841 detect artifact signals by sensing changes in the received signal out of range of a predetermined expected normal ECG from the same pair of electrodes used to derive the desired ECG signal; that is, between an electrode at a first ground or common location and an electrode at an ungrounded or uncommon location.

Holsinger U.S. Pat. No. 3,868,947 describes a multiple electrode system for artifact compensation and assumes a common mode artifact signal on the center electrodes of spaced coaxial electrode pairs in contact with the skin at spaced points with the outer annular electrode of each pair connected together and to a common ground of a differential amplifier having a pair of inputs respectively connected to respective ones of the center electrodes in a pair. This approach is of limited utility in solving the problem of detecting baseline shift because the causes of basline shift at the location of one pair of electrodes is not likely to produce the same baseline shift, if any, at a spaced pair of electrodes.

Accordingly, it is an important object of this invention to provide improved methods and means for detecting baseline shift in an ECG signal.

It is a further object of the invention to achieve the preceding object with apparatus that is relatively easy and inexpensive to fabricate and install while providing a relatively reliable indication of baseline shift with relatively little attention to the apparatus.

It is a further object of the invention to achieve one or more of the preceding objects while providing a useful signal.

It is a further object of the invention to achieve one or more of the preceding objects useful in automatic ECG monitoring systems helpful in avoiding erroneous alarm conditions.

SUMMARY OF THE INVENTION

According to the invention, there are first and second multielement electrode means attached to first and second surface portions of a patient, each electrode means having elements closely spaced but insulatedly separated, the ECG potential between the elements being negligible, there are first and second means for differentially combining, respectively, the potentials of one element from each of the multielement electrode means, and the potentials of the other element from each of the multielement electrode means, to provide first and second ECG signals, and means for differentially combining the ECG signals to provide an artifact signal representative of baseline shift.

Preferably, the first and second multielement electrode means are spaced by a distance greater than that between the elements of each of the electrode means, the distance between the elements is less than one inch, there are means for combining the ECG signals, and there is a third electrode means at a third patient surface portion, the differential combining means having a common input connected to it.

The method of the invention comprises positioning such multielement electrode portions on first and second patient surface portions, combining differentially the ECG potential of first elements from each multielement electrode and second the other elements from the multielement electrodes, to provide first and second ECG signals, and then differentially combining the two ECG signals to provide an artifact signal. Numerous other features, objects and advantages will become apparent from the following specifications when read in connection with the accompanying drawing in which:

Figure 1:
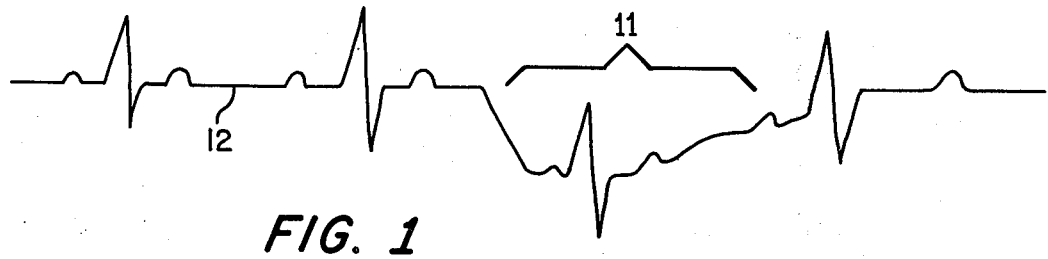
FIG. 1 is a graphical representation of an ECG signal indicating the occurrence of baseline-shift.

With reference now to the drawing and more particularly FIG. 1 thereof, there is shown a graphical representation of an ECG signal with baseline shift occurring in the interval of the third illustrated beat 11 where the baseline shifts below the normal baseline level 12.

Figure 2:
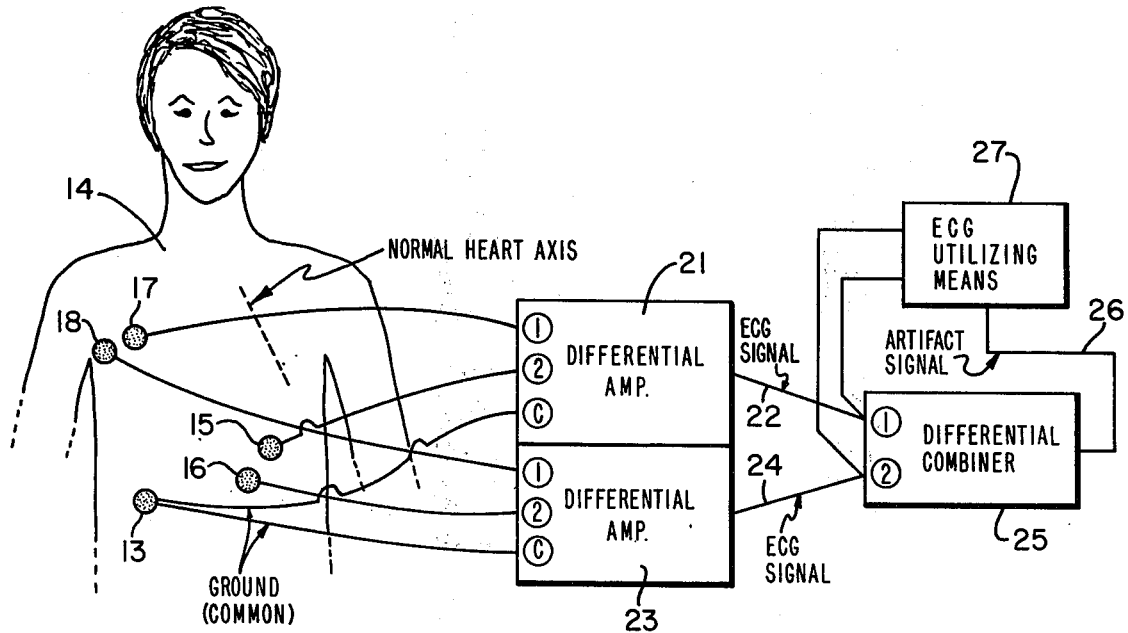
FIG. 2 is a combined block-diagram pictorial representation of an exemplary embodiment of a system according to the invention.

Referring to FIG. 2, there is shown a combined block pictorial representation of a system according to the invention for detecting baseline shift. The system includes a first ground, common or reference electrode 13 at a first surface location of patient 14 being monitored, a first pair of elements 15 and 16 of a multielement electrode at a second surface location of patient 14 and a second pair of elements 17 and 18 of another multielement electrode at a third surface location of patient 14. The spacing between elements 15 and 16 and between elements 17 and 18 is significantly less than the separation between the first location and each of the second and third locations and preferably that between the second and third locations. Typical separations between elements 17 and 18 and between elements 15 and 16 is one inch or less, and they are preferably arranged so that a line connecting their centers is perpendicular to the electrical axis of the heart. The separation between elements in a multielement electrode is small enough so that the ECG potential between them is negligible and large enough so that the motion of one electrode is at least partially independent of the motion of the other. The pairs of elements may be concentric as shown in Holsinger U.S. Pat. No. 3,868,947; however, the connections to external amplifying apparatus is different and as described below.

The systems includes a first.ECG differential amplifier 21 for providing a first ECG signal on line 22, and a second ECG differential amplifier 23 for providing a second ECG signal on line 24. It also includes a differential combiner 25, which need not be an amplifier, for providing an artifact signal on line 26. Differential combiner 25 receives the signals on lines 22 and 24. ECG utilizing means 27 receives the signals on lines 22, 24 and 26 and typically provides an alarm signal only when the ECG signal characterizes an unstable condition of patient 14, such as arrhythmia or an unacceptable heartbeat rate, while preventing the occurrence of an alarm signal when an artifact signal on line 26 occurs, signifying that a condition has occurred at an associated pair of elements producing a baseline shift.

The grounded, common or reference input C of each differential amplifier 21 and 23 is connected to reference electrode 13 at the first patient surface location. It is common practice to have a reference terminal such as 13 attached to the patient and connected to one or more common terminals of the amplifying means for reducing noise. The 1 and 2 signal inputs of first ECG differential amplifier 21 are connected to electrode elements 17 and 15, respectively, the elements being selected from different multielement electrodes at different patient locations. The 1 and 2 signal inputs of the second ECG differential amplifier 23 are connected to the other elements 18 and 16, respectively, of the different multielement electrodes.

Accordingly, two nearly identical ECG signals 22 and 24 from two multielement electrodes are produced. The difference between these two parallel ECG signals, as detected by differential combiner 25, is baseline shift, creating artifact signal 26.

The specific means for utilizing the ECG signals 22 and 24 and the artifact signal 26 is not a part of the invention. For example, it is possible to use either of the ECG signals 22 and 24 or to combine the two by summation to produce the true ECG. Or ECG utilizing means 27 may include, in addition, circuitry that responds to the occurrence of an artifact signal on line 26 for providing a signal that inhibits the alarm indicating circuitry. The ECG utilizing means might also or alternatively include circuitry for combining the artifact signal with the ECG signal to effectively restore the shifted baseline substantially to the normal baseline 12.

There has been described novel apparatus and techniques for detecting a baseline shift in an ECG signal. It is evident that those skilled in the art may now make numerous modifications and uses of and departures from the specific embodiment described herein without departing from the inventive concepts. Consequently, the invention is to be construed as embracing each and every novel feature and novel combination of features present in or possessed by the apparatus and techniques herein disclosed and limited solely by the spirit and scope of the appended claims.

What is claimed is:

1. Apparatus for providing an ECG signal and detecting baseline shift in said ECG signal comprising,
    a first multielement electrode means having elements closely spaced but insulatedly separated for connection to a first surface portion of a patient, the ECG.potential between said elements being negligible,
    a second multielement electrode means having elements closely spaced but insulatedly separated for connection to a second surface portion of said patient, the ECG potential between said elements being negligible,
    first means for differentially combining the potentials of one element of said first multielement electrode means and one element of said second multielement electrode means for providing a first ECG signal,
    second means for differentially combining the potentials of another element of said first multielement electrode means and another element of said second multielement electrode means for providing a second ECG signal,
    and means for differentially combining said first and second ECG signals to provide an artifact signal representative of baseline shift in said ECG signals.

2. Apparatus in accordance with claim 1 in which said first multielement electrode means is spaced from said second multielement electrode means by a distance significantly greater than the distance between elements of each of said multielement electrode means.

3. Apparatus in accordance with claim 1 further comprising a third electrode means at a third surface portion of said patient wherein each of said first and second differential combining means includes a common input connected to said third electrode means.

4. Apparatus in accordance with claim 1 wherein the spacing between said elements in each of said first and second multielement electrode means is less than one inch.

5. Apparatus in accordance with claim 1 further comprising means for combining said first and second ECG signals.

6. A method of providing an ECG signal and detecting baseline shift in said ECG signal comprising the steps of,
    positioning first and second closely spaced but insulatedly separated electrode portions in contact with a first surface portion of a patient so that in the absence of baseline shift the ECG potential therebetween is negligible, there being substantially a first ECG potential on both said electrode portions,
    positioning third and fourth closely spaced but insulatedly separated electrode portions in contact with a second surface portion of said patient so that in the absence of baseline shift the ECG potential therebetween is negligible, there being substantially a second ECG potential on both said electrode portions, differentially combining the potential of one of said first and second electrode portions with the potential of one of said third and fourth electrode portions to provide a first ECG signal, differentially combining the potential of the other of said first and second electrode portions with the potential of the other of said third and fourth electrode portions to provide a second ECG signal, and differentially combining said first and second ECG signals to provide an artifact signal representative of baseline shift in said ECG signals.

* * * * *